US010428039B2

(12) United States Patent
Gordillo et al.

(10) Patent No.: US 10,428,039 B2
(45) Date of Patent: Oct. 1, 2019

(54) PROCESS FOR PREPARING FURAN-2,5-DICARBOXYLIC ACID

(71) Applicant: BASF SE, Ludwigshafen am Rhein (DE)

(72) Inventors: Alvaro Gordillo, Heidelberg (DE); Martin Alexander Bohn, Mannheim (DE); Stephan A. Schunk, Heidelberg-Rohrbach (DE); Ivana Jevtovikj, Heidelberg (DE); Rene Backes, Lampertheim (DE); Holger Werhan, Rauenberg (DE); Svenia Duefert, Ludwigshafen (DE); Richard Dehn, Ludwigshafen (DE); Markus Piepenbrink, Telgte (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/773,411

(22) PCT Filed: Nov. 3, 2016

(86) PCT No.: PCT/EP2016/076525
§ 371 (c)(1),
(2) Date: May 3, 2018

(87) PCT Pub. No.: WO2017/076956
PCT Pub. Date: May 11, 2017

(65) Prior Publication Data
US 2018/0319758 A1 Nov. 8, 2018

(30) Foreign Application Priority Data
Nov. 4, 2015 (EP) .................. 15193065

(51) Int. Cl.
C07D 307/02 (2006.01)
C07D 307/46 (2006.01)
C07D 307/68 (2006.01)

(52) U.S. Cl.
CPC ......... *C07D 307/46* (2013.01); *C07D 307/68* (2013.01)

(58) Field of Classification Search
CPC ........................ C07D 307/46; C07D 307/68
USPC ........................................ 549/488
See application file for complete search history.

(56) References Cited

U.S. PATENT DOCUMENTS 8,242,293 B2 8/2012 Gruter et al.
8,877,950 B2 11/2014 Gruter et al.
2008/0103318 A1 5/2008 Lilga et al.
2015/0344394 A1 12/2015 Parvulescu et al.
2016/0008791 A1 1/2016 Schunk et al.
2016/0311684 A1 10/2016 Milanov et al.
2016/0312004 A1 10/2016 Wagner et al.
2016/0326347 A1 11/2016 Wagner et al.
2017/0080407 A1 3/2017 Schunk et al.
2017/0107166 A1 4/2017 Limbach et al.
2017/0217869 A1 8/2017 Limbach et al.
2017/0284251 A1 10/2017 Wang et al.
2017/0305871 A1 10/2017 Ohlmann et al.
2017/0333877 A1 11/2017 Titlbach et al.
2017/0354956 A1 12/2017 Koenig et al.
2018/0071679 A1 3/2018 Karpov et al.

FOREIGN PATENT DOCUMENTS

| CN | 104169264 A | * 11/2014 |
|---|---|---|
| EP | 2762470 A1 | 8/2014 |
| WO | 2009030512 A2 | 3/2009 |
| WO | 2009076627 A2 | 6/2009 |
| WO | 2009155297 A1 | 12/2009 |
| WO | 2011043661 A1 | 4/2011 |
| WO | 2013033081 A2 | 3/2013 |
| WO | 2015056270 A1 | 4/2015 |
| WO | 2015071138 A1 | 5/2015 |
| WO | 2015075540 A1 | 5/2015 |
| WO | 2015173295 A1 | 11/2015 |
| WO | 2015173296 A1 | 11/2015 |

(Continued)

OTHER PUBLICATIONS

Klrk Othmer editor, Esterification, Kirk-Othmer Encyclopedia of Chemical Technology, Feb. 2005, vol., 10, 5th ed, , p. 471-496. (Year: 2005).*

(Continued)

*Primary Examiner* — Taylor V Oh
(74) *Attorney, Agent, or Firm* — Armstrong Teasdale LLP

(57) ABSTRACT

Provided herein is a process for preparing furan-2,5-dicarboxylic acid. The process includes the following steps: (A-1) preparing a starting mixture comprising one, two or more carbohydrate compounds selected from the group consisting of: hexoses, oligosaccharides comprising hexose units, and polysaccharides including hexose units, and as a solvent or as a co-solvent for the carbohydrate compounds an amount of one or more carboxylic acid esters of a formula (II) and (A-2) subjecting the starting mixture to reaction conditions so that at least one of the one, two or more carbohydrate compounds reacts, and a fraction of the amount of one or more carboxylic acid esters of formula (II) is hydrolyzed, resulting in a mixture including 5-(hydroxymethyl)furfural and/or the one or more HMF esters of a formula (I), one or more carboxylic acids of a formula (III) and a remaining fraction of the amount of one or more carboxylic acid esters of formula (II).

19 Claims, 2 Drawing Sheets

(56) References Cited

FOREIGN PATENT DOCUMENTS

| WO | 2015173307 A1 | 11/2015 |
| WO | 2015197699 A1 | 12/2015 |
| WO | 2016050836 A1 | 4/2016 |
| WO | 2016096990 A1 | 6/2016 |
| WO | 2016206909 A1 | 12/2016 |
| WO | 2016207025 A1 | 12/2016 |
| WO | 2016207365 A1 | 12/2016 |
| WO | 2017005814 A1 | 1/2017 |
| WO | 2017012842 A1 | 1/2017 |
| WO | 2017025593 A1 | 2/2017 |
| WO | 2017076942 A1 | 5/2017 |
| WO | 2017076947 A1 | 5/2017 |

OTHER PUBLICATIONS

International Search Report and Written Opinion for International Application No. PCT/EP2016/076525, dated Dec. 21, 2016 9 pages.
Extended European Search Report dated Mar. 10, 2016 5 pages.

* cited by examiner

PROCESS FOR PREPARING FURAN-2,5-DICARBOXYLIC ACID

CROSS-REFERENCE TO RELATED APPLICATIONS

This application is the national stage entry of PCT/EP2016/076525, filed on Nov. 3, 2016, which claims the benefit of priority to European Patent Application No. 15193065.8, filed Nov. 4, 2015, which are incorporated by reference in their entirety herein.

FIELD OF INVENTION

The present invention relates to a process for preparing furan-2,5-dicarboxylic acid (FDCA). The invention also relates to a corresponding use of a specific carboxylic acid ester in such processes. The present invention is defined in the appended claims. Furthermore, preferred configurations and aspects of the present invention are apparent from the detailed description and the working examples. Also described is a process for preparing a mixture comprising 5-(hydroxymethyl)furfural (HMF) and one or more specific HMF esters.

5-(Hydroxymethyl)furfural (HMF) and derivatives thereof as well as furan-2,5-dicarboxylic acid (hereinafter FDCA) are important intermediate compounds for production of various products, for example surfactants, polymers and resins.

BACKGROUND

With increasing depletion of fossil feedstocks, starting materials based on renewable resources are needed, e.g. as alternatives to terephthalic acid (a compound used in the production of polyethylene terephthalate, PET). PET is based on ethylene and p-xylene which are usually obtained starting from of oil, natural gas or coal, i.e. from fossil fuels. While bio-based routes to ethylene (e.g. dehydration of bio-ethanol) are operated on commercial scale a straightforward access to bio-terephthalic acid remains difficult. FDCA is the best bio-based alternative to terephthalic acid (for further information see: Lichtenthaler, F. W., "*Carbohydrates as Organic Raw Materials*" in Ullmann's Encyclopedia of Industrial Chemistry, Wiley-VCH Verlag GmbH & Co. KGaA, Weinheim, 2010).

HMF is a versatile platform chemical. Alkoxymethylfurfurals, e.g. 2,5-furandicarboxylic acid, 5-hydroxymethylfuroic acid, bishydroxymethylfuran, 2,5-dimethylfuran, and the diether of HMF are furan derivatives with a high potential in fuel and/or polymer applications. Some important non-furanic compounds can also be produced from HMF, namely levulinic acid, adipic acid, 1,6-hexanediol, caprolactam, and caprolactone.

FDCA can be co-polymerized with mono-ethylene glycol to give polyethylene furanoate (PEF), a polyester with properties similar to PET.

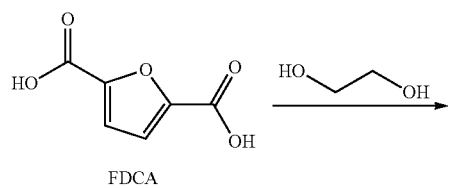

FDCA

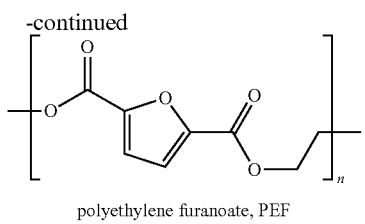

polyethylene furanoate, PEF

FDCA is usually obtained starting from fructose and/or other hexoses via a catalyzed, preferably acid-catalyzed, dehydration to key intermediate 5-(hydroxymethyl)furfural (HMF) followed by oxidation to FDCA. In literature, processes are disclosed where esters of HMF are used as precursors to prepare FDCA (e.g. U.S. Pat. No. 8,242,293 B2).

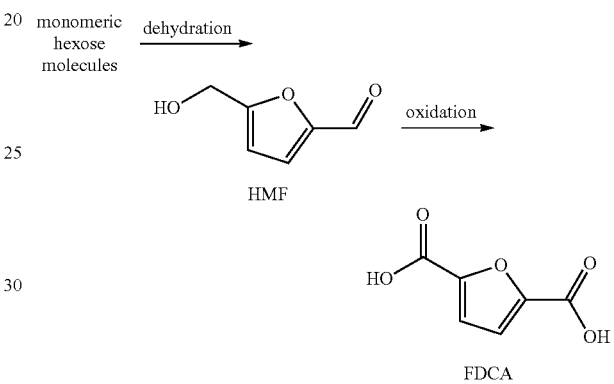

In the dehydration step by-products are formed, depending on the specific design of the process.

Typical by-products of this process are levulinic acid and formic acid (see scheme below) which are formed upon hydrolysis of HMF.

In processes for preparing a mixture comprising 5-(hydroxymethyl)furfural (HMF) (and one or more by-products) or in processes for preparing FDCA known in the prior art, a mixture comprising 5-(hydroxymethyl)furfural (HMF) is prepared by subjecting a material mixture, comprising one, two or more compounds selected from the group consisting of hexoses (monomeric hexose molecules, e.g. fructose), oligosaccharides comprising hexose units, and polysaccharides comprising hexose units, to reaction conditions so that a mixture comprising HMF, water and by-products (for example, levulinic acid and formic acid) results. Under the reaction conditions oligo- and/or polysaccharides are usually depolymerised, and subsequently the resulting monosaccharides, e.g. monomeric hexose molecules, are converted into HMF. Hexoses, oligosaccharides and polysaccharides are typically selected from the group consisting of fructose, glucose, and cellulose.

During depolymerisation oligo- or polysaccharides are usually converted into monomeric hexose molecules by hydrolytic cleavage of the ether bonds connecting the different hexose units in an oligo- or polysaccharide molecule (e.g. cellulose). The products of a typical depolymerization process (monomeric hexose molecules) are present in their aldehyde form.

Typically, according to routines at least in part previously undisclosed, depolymerization is conducted by using a catalyst, preferably in a one-pot-procedure. Typically a hydrophilic solvent is used (in particular water), e.g. in order to increase the amount of dissolved cellulose thus increasing the yield per process run. It is typically advantageous to conduct the conversion of cellulose into HMF by means of a heterogeneous catalyst in order to facilitate post-synthetic workup. In a typical depolymerization process, an aqueous solution is used as a solvent, sometimes comprising 50 wt.-% of water or more, based on the total weight of the depolymerization mixture used.

Alternatively, if monosaccharides are used as a starting material for preparing a mixture comprising HMF, water, and by-products, e.g. di-HMF (5,5'(oxy-bis(methylene))bis-2-furfural), no depolymerisation step is needed.

Monosaccharides produced or provided are typically subjected to a dehydration process, wherein the monomeric hexose molecule is typically transferred by isomerisation (via e.g. ketone-enone tautomerization) into its ketone form which is subsequently converted into its ring form. After ring closure, the formed ring-closed hexose molecules are typically dehydrated (and optionally further isomerised) resulting in a mixture comprising HMF, by-products (e.g. di-HMF) and water. However, water causes undesirable by-products due to hydrolysis of the formed HMF as described above (for example, humins, levulinic acid and formic acid).

Due to the insolubility of specific monomeric hexose molecules (e.g. fructose) in common organic solvents, a typical dehydration process step in the prior art is performed in an aqueous environment so that an aqueous solution comprising HMF and water is obtained as a (crude) mixture. As mentioned above, the presence of water leads to hydrolysis of HMF into by-products (e.g. levulinic acid and formic acid) and therefore decreases the overall yield of the reaction.

Isolation of HMF from such aqueous mixtures is challenging since HMF often undergoes side-reactions, e.g. hydrolysis (see scheme below).

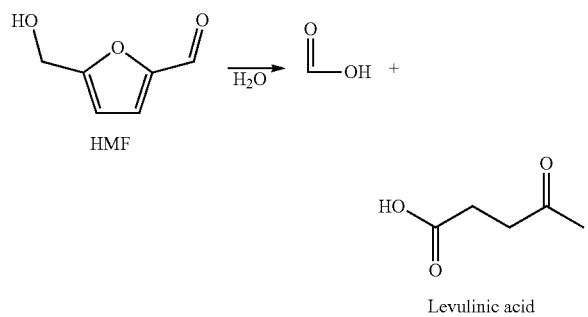

Hence, the (crude) mixture comprising HMF and water is usually contaminated with by-products to a certain degree and separation of HMF from the by-products is not possible with justifiable effort.

The aforementioned disclosures regarding the depolymerization or dehydration step also apply to (i) a process for preparing a mixture comprising 5-(hydroxymethyl)furfural (HMF) and one or more HMF esters and a corresponding process for preparing furan-2,5-dicarboxylic acid comprising the step of further processing said mixture and (ii) a use of a carboxylic acid ester in a process for preparing 5-(hydroxymethyl)furfural and HMF esters according to the present invention as described in detail hereinbelow or for preparing FDCA according to the present invention as described in detail hereinbelow. In particular, the successive steps of depolymerization and dehydration can be used to prepare a mixture as employed according to the present invention.

Different teachings regarding the isolation or preparation of FDCA or HMF, respectively, have been reported in the patent literature:

WO 2008/054804 A2 relates to "Hydroxymethyl furfural oxidation methods" (title). It is disclosed that a high solubility of FDCA in an acetic acid/water mixture (volume ratio 40:60) is achieved, compared to the solubility in pure water (cf. paragraph [0058]).

WO 2013/033081 A2 discloses a "process for producing both biobased succinic acid and 2,5-furandicarboxylic acid" (title).

US 2008/103318 discloses "hydroxymethyl furfural oxidation methods" (title) comprising the step of "providing a starting material which includes HMF in a solvent comprising water into reactor". The starting material is brought into contact "with the catalyst comprising Pt on the support material where the contacting is conducted at a reaction temperature of from about 50° C. to about 200° C.".

U.S. Pat. No. 8,877,950 B2 relates to a "method for the synthesis of 5-hydroxymethylfurfural ethers and their use" (title). HMF derivatives are made "by reacting a fructose and/or glucose-containing starting material with an alcohol in the presence of a catalytic or sub-stoichiometric amount of solid ("heterogeneous") acid catalyst" (see abstract).

U.S. Pat. No. 8,242,293 B2 relates to a "Method for the synthesis of organic acid esters of 5-hydroxymethylfurfural and their use" (title). The corresponding esters are disclosed to be "the condensation product of formic acid or its anhydride with HMF (formioxymethylfurfural), acetic acid or its anhydride with HMF (5-acetoxymethylfurfural), or of propionic acid or its anhydride with HMF (5-propionoxymethylfurfural)" (see column 1, lines 20-24) or of "(iso)-butyric acid" (see column 2, line 43) or of "(iso)butyric anhydride" (see column 2, line 47). Different catalysts have been employed in a corresponding process (see column 3, lines 1-31).

WO 2009/076627 A2 relates to the "conversion of carbohydrates to hydroxymethylfurfural (HMF) and derivatives" (title). A method is disclosed "for synthesizing HMF by contacting a carbohydrate source with a solid phase catalyst" (see claim 1). Furthermore, a method of preparing HMF esters is disclosed starting from a mixture "comprising a carbohydrate source, a carboxylic acid, with or without an added catalyst to provide a reaction mixture" (see claim 4).

WO 2011/043661 A1 relates to a "Method for the preparation of 2,5-furandicarboxylic acid and for the preparation of the dialkyl ester of 2,5-furandicarboxylic acid" (title). A method is disclosed "for the preparation of 2,5-furan dicarboxylic acid comprising the step of contacting a feed comprising a compound selected from the group consisting of 5-hydroxymethylfurfural ("HMF"), an ester of 5-hydroxymethylfurfural, 5-methylfurfural, 5-(chloromethyl)furfural, 5-methylfuroic acid, 5-(chloromethyl)furoic acid, 2,5-dimethylfuran and a mixture of two or more of these compounds with an oxidant in the presence of an oxidation catalyst at a temperature higher than 140° C." (see abstract). The oxidation catalyst comprises cobalt, manganese and/or a source of bromine (see claims 3 and 4).

WO 2009/030512 A2 relates to "hydroxymethylfurfural ethers and esters prepared in ionic liquids" (title). A method is disclosed "for the manufacture of an ether or ester of 5-hydroxymethylfurfural by reacting a hexose-containing starting material or HMF with an alcohol or an organic acid dissolved into an ionic liquid, using a metal chloride as catalyst" (see claim 1).

Related art are also WO 2015/075540 A1, WO 2009/155297 A1 and WO 2015/056270 A1.

DETAILED DESCRIPTION

Figure 1:
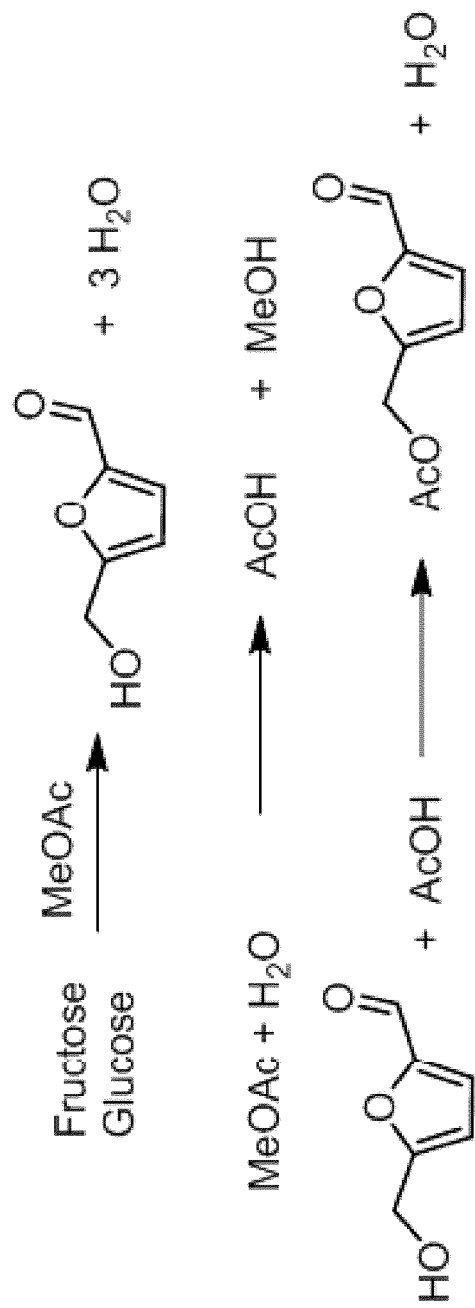
FIG. 1 is a schematic drawing of exemplary reactions taking place in an exemplary process of the present invention.

Despite the considerable efforts made by industry, there remains a need for further improvement. Thus, according to a first aspect it was an object of the present invention to provide an improved process for preparing furan-2,5-dicarboxylic acid (FDCA), which avoid or at least alleviates disadvantages of the processes known to date (and as stated above) and which can be operated in an economically advantageous manner. Preferred processes to be specified according to further aspects should favourably
- be capable to be conducted without the use of a dehydration catalyst and/or initial addition of acid,
- reuse by-products formed in the process,
- prevent side reactions,
- increase the yield of the overall process compared to processes known in the prior art,
- allow for a more convenient separation of by-products compared to processes known in the prior art, and/or
- allow to reduce the complexity of reactor set-ups known in the prior art.

This is achieved by the process of the invention.

The process of the invention is based on
(a) a process for preparing a mixture comprising 5-(hydroxymethyl)furfural (HMF) and one or more HMF esters of formula (I),

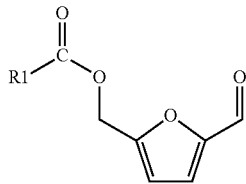

(I)

wherein in each of said HMF esters of formula (I), independently of each other, R1 is
(i) hydrogen
or
(ii) a substituted or unsubstituted, branched or linear, saturated or unsaturated or aromatic hydrocarbon radical having a total number of 21 carbon atoms or less, the process comprising the following steps:
(A-1) preparing or providing a starting mixture comprising
one, two or more carbohydrate compounds selected from the group consisting of hexoses, oligosaccharides comprising hexose units, and polysaccharides comprising hexose units,
and as the solvent or as a co-solvent for said carbohydrate compounds an amount of
one or more carboxylic acid esters of formula (II)

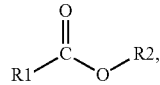

(II)

wherein in each of said carboxylic acid esters of formula (II)
R1 is the same as defined for formula (I) above and
R2 is a substituted or unsubstituted, branched or linear or cyclic, aliphatic hydrocarbon radical having a total number of 10 carbon atoms or less,
(A-2) subjecting said starting mixture to reaction conditions so that
at least one of said one, two or more carbohydrate compounds reacts,
and
a fraction of said amount of one or more carboxylic acid esters of formula (II) is hydrolyzed,
so that
a mixture results comprising
5-(hydroxymethyl)furfural and/or said one or more HMF esters of formula (I),
one or more carboxylic acids of formula (III)

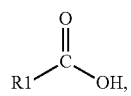

(III)

wherein R1 is the same as defined for formula (I) above,
one or more alcohols R2-OH, wherein R2 is the same as defined for formula (II) above,
and
a remaining fraction of said amount of one or more carboxylic acid esters of formula (II)

The process of the invention as defined in the claims, for preparing FDCA, correspondingly is
(b) a process for preparing furan-2,5-dicarboxylic acid, the process comprising the following steps:
(A-1) preparing or providing a starting mixture comprising
one, two or more carbohydrate compounds selected from the group consisting of hexoses, oligosaccharides comprising hexose units, and polysaccharides comprising hexose units,
and as the solvent or as a co-solvent for said carbohydrate compounds an amount of
one or more carboxylic acid esters of formula (II)

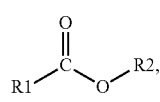

(II)

wherein in each of said carboxylic acid esters of formula (II)
R1 is the same as defined for formula (I) above and R2 is a substituted or unsubstituted, branched or linear or cyclic, aliphatic hydrocarbon radical having a total number of 10 carbon atoms or less, (A-2) subjecting said starting mixture to reaction conditions so that at least one of said one, two or more carbohydrate compounds reacts, and a fraction of said amount of one or more carboxylic acid esters of formula (II) is hydrolyzed, so that a mixture results comprising 5-(hydroxymethyl)furfural and/or said one or more HMF esters of formula (I)

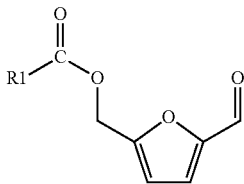

(I)

wherein in each of said HMF esters of formula (I), independently of each other, R1 is (i) hydrogen or (ii) a substituted or unsubstituted, branched or linear, saturated or unsaturated or aromatic hydrocarbon radical having a total number of 21 carbon atoms or less, one or more carboxylic acids of formula (III)

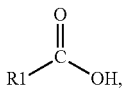

(III)

wherein R1 is the same as defined for formula (I) above, one or more alcohols R2-OH, wherein R2 is the same as defined for formula (II) above, and a remaining fraction of said amount of one or more carboxylic acid esters of formula (II), (B-1) subjecting said mixture resulting in step (A-2)

or a mixture comprising 5-(hydroxymethyl)furfural and/or one or more HMF esters of formula (I) obtained from said mixture resulting in step (A-2) by additional treatment steps to oxidation conditions so that a product mixture results comprising furan-2,5-dicarboxylic acid and one or more carboxylic acids of formula (III).

In a process according to the invention as described above or below, carboxylic acid esters of formula (II) in step (A-1) is present as the solvent or as a co-solvent for said carbohydrate compounds, in step (A-2) a fraction of said amount of one or more carboxylic acid esters of formula (II) is hydrolyzed. Thus, in a process according to the invention as described above or below, carboxylic acid esters of formula (II) have the function of a "reactive solvent". A reactive solvent acts as both (i) a reactant and (ii) a solvent. As a reactant, in step (A-2) the carboxylic acid esters of formula (II) react with water (formed in-situ or present in the starting mixture of step (A-1)) to form carboxylic acids of formula (III) which can then further react with HMF to form HMF esters of formula (I). As a (co-)solvent, in steps (A-1) and (A-2) the carboxylic acid esters of formula (II) contribute to keeping in solution said one, two or more carbohydrate compounds, in the starting mixture. Furthermore, the remaining fraction of carboxylic acid esters of formula (II) typically contributes to keeping in solution the products (HMF and/or HMF esters of formula (I)) present in the mixture resulting in step (A-2).

In many industrial cases, it is preferred to employ alkyl formates of the formula R2-O—C(=O)H (as for alternative (i), meaning R1=H) as they are readily available. However, in other cases, where R1 is a hydrocarbon radical as defined herein above or below (as for alternative (ii)), the corresponding carboxylic acid esters of formula (II) are preferred over said alkyl formates of the formula R2-O—C(=O)H.

As stated above, in a process as described above for preparing furan-2,5-dicarboxylic acid said mixture as obtained in step A-2 is further processed by the following step (B-1):

(B-1) subjecting said mixture resulting in step (A-2)

or a mixture comprising 5-(hydroxymethyl)furfural and/or one or more HMF esters of formula (I) obtained from said mixture resulting in step (A-2) by additional treatment steps to oxidation conditions so that a product mixture results comprising furan-2,5-dicarboxylic acid and one or more carboxylic acids of formula (III).

All specific or general aspects and all statements regarding preferred embodiments or features which apply to step (A) (with sub-steps (A-1), (A-2), etc) of the process according to the present invention, i.e. which apply to the step for preparing a mixture comprising 5-(hydroxymethyl)furfural (HMF) and one or more HMF esters of formula (I) as described herein (in particular if described as being preferred)

also apply, mutatis mutandis, to the overall process according to the present invention for preparing furan-2,5-dicarboxylic acid, and vice versa.

In particular, in each specific aspect of the present invention and all statements regarding preferred embodiments or features, group R1 is the same in the compounds of formula (I), (II) and (III). The meaning of R1 may differ for different specific aspects and all statements regarding preferred embodiments or features of the present invention.

Similarly, in each specific aspect of the present invention and all statements regarding preferred embodiments or features, group R2 is the same in the compounds of formula (II) and alcohol R2-OH. The meaning of R2 may differ for different specific aspect and all statements regarding preferred embodiments or features of the present invention.

If not indicated otherwise, the "total number" of carbon atoms in a specified radical is the total number in the radical including any substituents. I.e., when counting the total number of carbon atoms in a substituted radical the carbon atoms in the substituent are also counted.

In step (A-2), the term "reaction conditions" indicates conditions causing (a) said carbohydrate compounds to react so that 5-(hydroxymethyl)furfural (HMF) and/or (by reaction of HMF) said one or more HMF esters of formula (I) are generated and (b) hydrolysis of a fraction of said amount of one or more carboxylic acid esters of formula (II) so that said carboxylic acids of formula (III) and said alcohols R2-OH are formed, The reaction mechanism involved is described in more detail below, in particular with reference to exemplary processes.

In step (B-1), the term "oxidation conditions" indicates conditions suitable for causing both HMF and HMF esters of formula (I) to react and to give said product mixture comprising furane-2,5-dicarboxylic acid and one or more carboxylic acids of formula (III).

As stated above, dehydration of fructose is often conducted in an aqueous medium. Beside the intrinsic problem of conducting dehydration reactions in aqueous media, water can lead to several by-products (see for example Tian et al., Chem. Commun., 2013, 49, pages 8668-8670). As water is produced in the dehydration of fructose to HMF, even under initially non-aqueous reaction conditions, the water content increases with reaction time. The challenges and problems of prior art process are summarized in, e.g. EP 2 762 470 A1 which relates to "the synthesis and recovery of substantially pure HMF and derivatives thereof from hexose carbohydrate feedstocks" (see [0002]). The document explicitly mentions that "a method which provides HMF with good selectivity and in high yields has yet to be found" and which does not yield "by-products, such as, levulinic and formic acids" (see [0008]). In contrast thereto, a process according to the present invention produces HMF and HMF esters of formula (I) or furane-2,5-dicarboxylic acid (FDCA) with high selectivities and low by-product formation. In a process according to the present invention carboxylic acid esters of formula (II) act and are deliberately used as a dehydration agent which reacts with water, resulting in the formation of one or more carboxylic acids of formula (III) and one or more alcohols R2-OH (see, for example, the corresponding reaction in FIG. 1).

Moreover, concurrent with the reaction of carbohydrate compounds to HMF and/or HMF esters of formula (I) in the presence of one or more carboxylic acid esters of formula (II), one or more carboxylic acids of formula (III) (see step (A-2)) are produced which act as a solvent in the oxidation reaction of step (B-1) according to the present invention.

Under the reaction conditions of step (A-2) said one or more carboxylic acid esters of formula (II) react with water (present in the starting mixture prepared or provided in step (A-1) and/or produced by the dehydration of carbohydrate compounds in step (A-2)) to give one or more carboxylic acids of formula (III) and one or more alcohols R2-OH. Thus, the negative effect of the side reactions typically caused by the presence of water (see the above discussion of prior art processes) is avoided or at least alleviated.

The reaction products of the reaction of said one or more carboxylic acid esters of formula (II) with water, i.e. said carboxylic acid of formula (III) and the alcohol R2-OH, surprisingly do not cause disadvantageous side reactions as observed for water, and thus contribute to an increase of the overall yield in HMF, HMF esters of formula (I) and, if applicable, FDCA in comparison to processes of the prior art. Alcohol R2-OH as well as carboxylic acid esters of formula (II) are also more conveniently separated from the mixture resulting in step (A-2) than, for example, water.

The formation of HMF esters of formula (I) is advantageous since it protects the hydroxyl group of the HMF and thus prevents dimerization or even polymerization of HMF (leading to humins). Furthermore, HMF esters of formula (I) can be oxidized to FDCA in the same manner as HMF.

The carboxylic acids of formula (III) formed in the process of the invention serve as (co-)solvents for the carbohydrate compounds in step (A-2) and for HMF and HMF esters of formula (I) in step (B-1). Thus, in contrast to the prior art, in processes according to the present invention organic acids or other corrosive compounds, typically used as solvents, do not need to be initially present in the starting mixture prepared or provided in step (A-1), and do not need to be added in a separate step. Therefore, no storage units or additional handling of these corrosive compounds is necessary.

Preferred are processes of the present invention as described herein above or below, wherein in the mixture resulting in step (A-2) the total amount of 5-(hydroxymethyl)furfural and HMF esters of formula (I) is in the range of from 0.5 to 50 wt.-%, preferably in the range of from 1 to 40 wt.-%, more preferably in the range of from 5 to 30 wt.-%, based on the total weight of the mixture resulting in step (A-2).

The upper limit for the total amount of 5-(hydroxymethyl)furfural and HMF esters of formula (I) is determined by their maximum solubility in carboxylic acid esters of formula (II).

If in the mixture resulting in step (A-2) the total amount of 5-(hydroxymethyl)furfural and HMF esters of formula (I) is below the lower limit of the ranges as indicated, the overall process can hardly be conducted in an efficient and economic manner.

Processes of the present invention as described above or below (or as described above as being preferred) are preferred, wherein the total weight of the one, two or more carbohydrate compounds in the starting mixture prepared or provided in step (A-1) is in the range of from 1 to 70 wt.-%, preferably in the range of from 5 to 60 wt.-%, more preferably in the range of from 10 to 50 wt.-%, based on the total weight of the starting mixture.

If the total weight of the one, two or more carbohydrate compounds in the starting mixture prepared or provided in step (A-1) is above the upper limit of the ranges as indicated, by-product formation becomes increasingly troublesome. If the total weight of the one, two or more carbohydrate compounds in the starting mixture prepared or provided in step (A-1) is below the lower limit of the ranges as indicated, the overall process can hardly be conducted in an efficient and economic manner.

In particular, processes of the present invention as described above or below are preferred, wherein the starting mixture prepared or provided in step (A-1) comprises fructose and glucose.

Fructose and glucose are preferred carbohydrate compounds in the starting mixture prepared or provided in step (A-1) as they are monomeric hexoses and thus do not need to be depolymerised as, for example, oligosaccharides comprising hexose units, or polysaccharides comprising hexose units.

Also preferred are processes of the present invention as described above or below wherein the starting mixture prepared or provided in step (A-1) does not comprise $NH_4Cl$.

If $NH_4Cl$ is used in a process according to the present invention side-product formation is observed, e.g. formation of 5-(chloromethyl)furfural.

In particular, processes of the present invention as described above or below are preferred, wherein the starting mixture prepared or provided in step (A-1) does not comprise any protic chloride salt.

Protic chloride salts often have the disadvantage of causing side-product formation as in the case of $NH_4Cl$ above. This may cause side-product formation and thus may lower the yield of the overall reaction to FDCA.

In many cases, processes of the present invention as described above or below are preferred, wherein the starting mixture prepared or provided in step (A-1) does not comprise any protic nitrogen-containing cation.

Protic nitrogen-containing cations often have the disadvantage of causing side-product formation as in the case of $NH_4Cl$ above. This may cause side-product formation and thus may lower the yield of the overall reaction to FDCA.

Preferred are processes of the present invention as described above or below, wherein the starting mixture prepared or provided in step (A-1) does not comprise any protic halide salt.

Similarly, as explained for protic chloride salts, protic halide salts in general often have the disadvantage of causing side-product formation. These acids cause side-product formation and thus lower the yield of the overall reaction to FDCA.

Preferred are processes of the present invention as described above or below, wherein the mixture resulting in step (A-2) does not comprise 5-(chloromethyl)furfural in an amount of 1 wt % or more. Preferably, the mixture resulting in step (A-2) does not comprise any 5-(chloromethyl)furfural.

The skilled person limits or avoids the formation of 5-(chloromethyl)furfural by limiting or avoiding the presence of any protic chloride salt, preferably by limiting or avoiding the presence of chloride in the starting mixture prepared or provided in step (A-1). Under reaction conditions as in step (A-2) of the present invention, 5-(chloromethyl)furfural reacts with HMF forming HMF dimers (5,5' (oxy-bis(methylene))bis-2-furfural) thus de-creasing the yield in HMF or HMF esters of formula (I) in step (A-2) of the present invention.

Preferred are processes of the present invention as described above or below, wherein the starting mixture prepared or provided in step (A-1) comprises
less than 35 wt % of water,
preferably less than 20 wt % of water,
more preferably less than 10 wt % of water,
even more preferably less than 1 wt % of water,
most preferably less than 0.1 wt % of water,
based on the total weight of the starting mixture.

It is advantageous if the starting mixture prepared or provided in step (A-1) comprises only a small amount of water which is consumed by directly hydrolysing said carboxylic acid esters of formula (II) and thus does not cause any disadvantageous side-reaction as in prior art processes discussed above.

Preferred are processes of the present invention as described above or below, wherein the starting mixture prepared or provided in step (A-1) has an acid value below 50, preferably below 5, more preferably below 1.

In a process of the invention, no acid needs to be added to the starting mixture prepared or provided in step (A-1) and thus no storage units or additional handling of these corrosive compounds is necessary.

Preferred are processes of the present invention as described above or below, wherein the starting mixture prepared or provided in step (A-1) comprises a total amount of carboxylic acid esters of formula (II) of at least 10 wt.-%, preferably at least 30 wt.-%, more preferably at least 50 wt.-%, based on the total weight of the starting mixture.

Depending on the amount of water and carbohydrate compounds present in the starting mixture prepared or provided in step (A-1) at least 10 wt.-% of carboxylic acid esters of formula (II) should be present in said mixture to produce enough carboxylic acids of formula (III) that can be used as (co-)solvent in step (B-1).

Preferred are processes of the present invention as described above or below, wherein in the mixture resulting in step (A-2) the molar ratio of the amount of 5-(hydroxymethyl)furfural to the total amount of HMF esters of formula (I) is in the range of from 100 to 0.001, preferably in the range of from 50 to 0.05, more preferably in the range of from 10 to 0.1.

The person skilled in the art identifies the corresponding reaction conditions by, e.g., a small series of pre-experiments. For example, in such a series of pre-experiments, he changes the reaction temperature (and/or reaction time) and measures the ratio of HMF to the total amount of HMF esters of formula (I) in the resulting product mixture.

In mixtures resulting in step (A-2) with a molar ratio of the amount of 5-(hydroxy-methyl)furfural to the total amount of HMF esters of formula (I) as described above, less by-products are formed in the oxidation reaction in step (B-1).

Preferred are processes of the present invention as described above or below, wherein in step (A-2) the reaction temperature is for at least 10 minutes
in the range of from 70° C. to 300° C.,
preferably in the range of from 140° C. to 260° C.,
more preferably in the range of from 160° C. to 240° C.,
even more preferably in the range of from 185° C. to 220° C.
and/or
wherein in step (A-2) the reaction temperature is in the range of from 185° C. to 220° C.
for at least 10 minutes,
preferably for at least 30 min,
more preferably for at least 1 hour.

It has been reported in literature (Jing and Xiuyang, Chin. J. Chem. Eng., Vol. 16, No. 6, 2008, page 893) that in glucose decomposition in aqueous media the "maximum yield of 5-HMF reached 32.0% in 30 min" (see section 3.4) and "5-HMF further degraded to formic acid, levulinic acid, and humic matter" (see section "conclusion"). However, in a process according to the present invention, the side reaction caused by water is reduced or prevented even if the reaction time is as short as 10 minutes.

Particularly, processes of the present invention as described above or below are preferred, wherein said one or at least one, preferably all, of said more alcohols R2-OH
(i) has a vapor pressure of at least 0.1 kPa at 25° C., preferably at least 1 kPa at 25° C., more preferably at least 3.2 kPa at 25° C., even more preferably at least 4 kPa at 25° C., particularly more preferably at least 5 kPa at 25° C.
and/or
(ii) is selected from the group consisting of:
methanol (R2=$CH_3$),
ethanol (R2=$CH_2CH_3$),
1-propanol (R2=$CH_2CH_2CH_3$),
2-propanol (R2=$CH(CH_3)_2$),
1-butanol (R2=$CH_2CH_2CH_3$),
2-butanol (R2=$CH(CH_3)CH_2CH_3$),
1-hydroxy-2-methylpropan (R2=$CH_2CH(CH_3)_2$),
2-hydroxy-2-methylpropan (R2=$C(CH_3)_3$),
and
2-Methoxyethanol (R2=$CH_2CH_2OCH_3$).

Specific alcohols R2-OH as described in the specific aspect above are particularly conveniently separated from the mixture resulting in step (A-2) due to their relatively low vapour pressures.

As mentioned above, in this specific aspect of the present invention and in all corresponding statements regarding preferred embodiments or features, group R2 is the very same in the compounds of formula (II) and alcohol R2-OH.

Due to the intrinsic chemistry of a process of the invention, group R2 as provided in carboxylic acid esters of formula (II) in the resulting mixture of step (A-2) is present in alcohol R2-OH.

Processes of the present invention as described above or below are preferred, wherein R1 is
(i) hydrogen
or
(ii) a linear or branched, saturated or unsaturated hydrocarbon radical having 15 carbon atoms or less,
more preferably a linear or branched, saturated or unsaturated hydrocarbon radical having 8 carbon atoms or less,
even more preferably a linear or branched, aliphatic radical having 6 carbon atoms or less,
particularly more preferably —$CH_3$, —$CH_2CH_3$, —CH($CH_3$)$_2$, —C($CH_3$)$_3$, —$CH_2CH_2CH_3$, or —$CH_2CH_2CH_2CH_3$,
most preferably —$CH_3$.

As mentioned above, in this specific aspect of the present invention and in all corresponding statements regarding preferred embodiments or features, group R1 is the very same in the compounds of formula (I), (II) and (III).

In a process of the present invention, the specific meaning of R1 as defined according to this aspect is preferred as the corresponding carboxylic acids of formula (III) can be conveniently separated (e.g. by means of distillation) from FDCA in a purification step (e.g. a distillation step). We refer to the description below regarding preferred processes of the present invention for preparing furan-2,5-dicarboxylic acid.

In many industrial cases, it is preferred to employ alkyl formates of the formula R2-O—C(=O)H (as for alternative (i), meaning R1=H) as they are readily available. However, in other cases, where R1 is a hydrocarbon radical as defined herein above or below (as for alternative (ii)), the corresponding specific carboxylic acid esters of formula (II) as defined in the specific aspect above are preferred over said alkyl formates of the formula R2-O—C(=O)H.

Due to the intrinsic chemistry of a process of the invention, group R1 as provided in carboxylic acid esters of formula (II) in the resulting mixture of step (A-2) is present in the carboxylic acids of formula (III) and is present in HMF esters of formula (I).

Correspondingly, said one or at least one, preferably all, of said more carboxylic acids of formula (III)

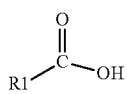

(III)

is preferably selected from the group consisting of:
formic acid (R1=H); preferred in specific industrial cases,
acetic acid (R1=$CH_3$),
propanoic acid (R1=$CH_2CH_3$),
butanoic acid (R1=$CH_2CH_2CH_3$),
2-methylpropanoic acid (R1=CH($CH_3$)$_2$),
2,2-dimethylpropanoic acid (R1=C($CH_3$)$_3$),
and
pentanoic acid (R1=$CH_2CH_2CH_2CH_3$),
is more preferably selected from the group consisting of:
acetic acid (R1=$CH_3$),
propanoic acid (R1=$CH_2CH_3$),
butanoic acid (R1=$CH_2CH_2CH_3$),
2-methylpropanoic acid (R1=CH($CH_3$)$_2$),
2,2-dimethylpropanoic acid (R1=C($CH_3$)$_3$),
and
pentanoic acid (R1=$CH_2CH_2CH_2CH_3$),
and most preferably said one or at least one of said more carboxylic acids of formula (III) acetic acid (R1=$CH_3$).

As mentioned above, in this specific aspect of the present invention and in all corresponding statements regarding preferred embodiments or features, group R1 is the very same in the compounds of formula (I), (II) and (III).

Due to the intrinsic chemistry of a process of the invention, group R1 as provided in carboxylic acid esters of formula (II) in the resulting mixture of step (A-2) is present in the carboxylic acids of formula (III) and is present in HMF esters of formula (I).

In many cases, processes of the present invention as described above or below are preferred, wherein in said one or at least one or preferably all of said more carboxylic acid esters of formula (II)
R1 is
(i) hydrogen (preferred in specific industrial cases)
or
(ii) a linear or branched, saturated or unsaturated hydrocarbon radical having 15 carbon atoms or less,
more preferably a linear or branched, saturated or unsaturated hydrocarbon radical having 8 carbon atoms or less,
even more preferably a linear or branched, aliphatic radical having 6 carbon atoms or less,
and independently thereof
R2 is
a substituted or unsubstituted, branched or linear or cyclic, alkyl radical having a total number of 10 carbon atoms or less,
preferably a substituted or unsubstituted, branched or linear or cyclic, alkyl radical having a total number of 6 carbon atoms or less,
more preferably a unsubstituted alkyl radical selected from the group consisting of methyl, ethyl, prop-1-yl, propan-2-yl, butan-1-yl, butan-2-yl, pentan-1-yl, pentan-2-yl, pentan-3-yl, 2-methylpropan-1-yl, 2-methylpropan-2-yl, 2-methylbutan-1-yl, 3-methylbutan-1-yl, 2-methylbutan-2-yl, 3-methylbutan-2-yl, cyclopentyl, and cyclohexyl,
even more preferably methyl.

In some industrial cases, it is preferred to employ alkyl formates of the formula R2-O—C(=O)H (as for alternative (i), meaning R1=H) as they are readily available. However, in other cases, where R1 is a hydrocarbon radical as defined herein above or below (as for alternative (ii)), the corresponding specific carboxylic acid esters of formula (II) as defined in the specific aspect above are preferred over said alkyl formates of the formula R2-O—C(=O)H.

Carboxylic acid esters of formula (II) as defined above for this specific aspect are preferred as they are readily available and have a relatively low vapor pressure. Such carboxylic acid esters of formula (II) with a low vapor pressure can be conveniently separated after step (A-2) from the mixture resulting in step (A-2), e.g. by means of distillation.

As mentioned above, in this specific aspect of the present invention and in all corresponding statements regarding preferred embodiments or features, group R1 is the very same in the compounds of formula (I), (II) and (III).

Similarly, in this specific aspect of the present invention and in all corresponding statements regarding preferred embodiments or features, group R2 is the very same in the compounds of formula (II) and alcohol R2-OH.

Due to the intrinsic chemistry of a process of the invention, group R1 as provided in carboxylic acid esters of formula (II) in the resulting mixture of step (A-2) is present in the carboxylic acids of formula (III) and is present in HMF esters of formula (I), and similarly group R2 as provided in carboxylic acid esters of formula (II) in the resulting mixture of step (A-2) is present in alcohol R2-OH.

Moreover, processes of the present invention as described above or below are particularly preferred, wherein said one or at least one, preferably all, of said more carboxylic acid esters of formula (II) is selected from the group consisting of methyl formate, ethyl formate, butyl formate methyl acetate, ethyl acetate, and butyl acetate, preferably selected from the group consisting of methyl acetate, ethyl acetate, and butyl acetate, more preferably methyl acetate.

Carboxylic acid esters of formula (II) as defined above for this specific aspect are particularly preferred as they are readily available and have a relatively low vapor pressure. Such carboxylic acid esters of formula (II) with a low vapor pressure can be conveniently separated after step (A-2) from the mixture resulting in step (A-2), e.g. by means of distillation.

In some industrial cases it is preferred to employ alkyl formates of the formula R2-O—C(=O)H (as for alternative (i), meaning R1=H) as they are readily available. However, in other cases, where R1 is hydrocarbon radical as defined herein above or below (as for alternative (ii)), the corresponding specific carboxylic acid esters of formula (II) as defined in the specific aspect above are preferred over said alkyl formates of the formula R2-O—C(=O)H.

As mentioned above, in this specific aspect of the present invention and in all corresponding statements regarding preferred embodiments or features, group R1 is the very same in the compounds of formula (I), (II) and (III).

Similarly, in this specific aspect of the present invention and in all corresponding statements regarding preferred embodiments or features, group R2 is the very same in the compounds of formula (II) and alcohol R2-OH.

Due to the intrinsic chemistry of a process of the invention, group R1 as provided in carboxylic acid esters of formula (II) in the resulting mixture of step (A-2) is present in the carboxylic acids of formula (III) and is present in HMF esters of formula (I), and similarly group R2 as provided in carboxylic acid esters of formula (II) in the resulting mixture of step (A-2) is present in alcohol R2-OH.

Processes of the present invention as described above or below are preferred, wherein said one or at least one, preferably all, of said more HMF esters of formula (I) is 5-(formoxymethyl)furfural (R1 is hydrogen) or 5-(acetoxymethyl)furfural (R1 is methyl), preferably 5-(acetoxymethyl)furfural (R1 is methyl).

In some industrial cases it is preferred to employ alkyl formates of the formula R2-O—C(=O)H (as for alternative (i), meaning R1=H) in the starting mixture prepared or provided in step (A-1) as they are readily available, and correspondingly 5-(formoxymethyl)furfural (R1 is hydrogen) is a preferred HMF ester of formula (I) produced in step (A-2). However, in other cases, where R1 is a hydrocarbon radical as defined herein above or below (as for alternative (ii)), the corresponding specific carboxylic acid esters of formula (II) as defined in the specific aspect above are preferred over said alkyl formates of the formula R2-O—C(=O)H.

5-(Acetoxymethyl)furfural is a preferred HMF ester of formula (I) as it can be oxidized conveniently to FDCA in a similar manner as HMF.

As mentioned above, in this specific aspect of the present invention and in all corresponding statements regarding preferred embodiments or features, group R1 is the very same in the compounds of formula (I), (II) and (III).

Due to the intrinsic chemistry of a process of the invention, group R1 as provided in carboxylic acid esters of formula (II) in the resulting mixture of step (A-2) is present in the carboxylic acids of formula (III) and is present in HMF esters of formula (I).

Processes of the present invention as described above or below are also preferred, wherein in step (A-2) said starting mixture is subjected to said reaction conditions in a pressurized reactor, wherein the pressure in the reactor at least temporarily is in the range of from 1 to 100 bar, preferably in the range of from 1 to 50 bar.

Subjecting said starting mixture in step (A-2) to said reaction conditions mixture in step (A-2) in a pressurized reactor is preferred as higher reaction temperatures can be reached in a pressurized reactor and thus the reaction accelerated.

Furthermore, processes of the present invention as described above or below are preferred, wherein the molar ratio of the total amount of said carboxylic acid esters of formula (II) present in the starting mixture prepared or provided in step (A-1)

to the total amount of water (i) present in the starting mixture prepared or provided in step (A-1)

and (ii) produced in step (A-2) by reaction of said carbohydrate compounds selected from the group consisting of hexoses, oligosaccharides comprising hexose units, and polysaccharides comprising hexose units is above 1, preferably above 1.2.

Starting mixtures prepared or provided in step (A-1) having a molar ratio of the total amount of said carboxylic acid esters of formula (II) to the total amount of water present in (i) and produced in (ii) of more than 1 prevent or at least reduce the hydrolysis of HMF to levulinic and formic acid because all the water is reacted with said carboxylic acid esters of formula (II).

Processes of the present invention as described above or below are preferred, wherein the mixture resulting in step (A-2) is non-aqueous or in the mixture resulting in step (A-2) the molar ratio of the total amount of the remaining fraction of said amount of one or more carboxylic acid esters of formula (II) to water is above 1.

Preferably, the non-aqueous mixture resulting in step (A-2) comprises less than 0.1 wt % of water, based on the total weight of the mixture.

Mixtures resulting in step (A-2), which have a molar ratio of the total amount of the remaining fraction of said amount of one or more carboxylic acid esters of formula (II) to the total amount of water of more than 1, prevent or reduce the hydrolysis of HMF to levulinic and formic acid as all the water (present in (i) and produced in (ii)) is further reacted with said carboxylic acid esters of formula (II). Moreover, the remaining fraction after step (A-2) can be used for preparing a starting mixture as in step (A-1).

Processes of the present invention as described above or below are preferred, wherein said starting mixture prepared or provided in step (A-1) comprises water, wherein (in said starting mixture)
the molar ratio of
the total amount of said carboxylic acid esters of formula (II) to water
is above 3, preferably above 5.

Aqueous starting mixtures prepared or provided in step (A-1), which have a molar ratio of the total amount of said carboxylic acid esters of formula (II) to water of more than 1, prevent or reduce the hydrolysis of HMF to levulinic and formic acid because all the water present is further reacted with said carboxylic acid esters of formula (II).

Preferably, processes of the present invention as described above or below are processes, wherein said starting mixture prepared or provided in step (A-1) comprises water, wherein in said starting mixture
the molar ratio of the total amount of
said carboxylic acid esters of formula (II)
to
the sum of
(i) the total amount of water
plus
(ii) three times the total amount of hexoses and hexose units
is above 1, preferably above 1.2.

In a starting mixture prepared or provided in the dehydration step (A-1), three water molecules are produced per hexose unit. Therefore, the hydrolysis of HMF to levulinic and formic acid can only be prevented if all the water present (i) and in-situ produced (ii) further reacts with said carboxylic acid esters of formula (II).

Processes of the present invention as described above or below comprising the following step are preferred:
in step (A-1) preparing said starting mixture by mixing
an aqueous feed mixture comprising said one, two or more carbohydrate compounds selected from the group consisting of hexoses, oligosaccharides comprising hexose units, and polysaccharides comprising hexose units,
with
said one or more carboxylic acid esters of formula (II).

Mixtures comprising carbohydrate compounds typically are aqueous. As the water contained in said mixtures comprising carbohydrate compounds can cause disadvantageous side-reactions as described above in prior art processes said water had to be separated from said mixtures comprising carbohydrate compounds. Thus, it is an achievement of the present invention that an aqueous starting mixture can be provided or prepared in step (A-1) and subjected to reaction conditions in step (A-2), without causing any disadvantages.

Processes of the present invention as described above or below are preferred, wherein none of said one or more carboxylic acid esters of formula (II) is ethyl oxalate, ethyl maleate, ethyl levulinate, methyl oxalate, methyl maleate or methyl levulinate.

Furthermore, processes of the present invention as described above or below are preferred, wherein the starting mixture prepared or provided comprises a catalytically effective amount of one, two or more catalysts being an alkali halide, preferably a sodium halide or lithium halide, more preferably selected from the group consisting of:
LiCl,
LiBr,
NaCl
and
NaBr.

A preferred catalytically effective amount of catalyst is a total amount of 20 ppm or more of said catalysts by weight based on the total weight of said one, two or more carbohydrate compounds in the reaction mixture of step (A-2).

Alkali halides as described above catalyze the formation of HMF and do not lead to side-product formation (e.g. 5-(chloromethyl)furfural or furfural) as it is observed when using $NH_4Cl$ as a catalyst.

Particularly preferred is a process according to the present invention as described above or below, wherein said
one or more carboxylic acid esters of formula (II)

present in said starting mixture prepared or provided in step (A-1) is prepared in a separate reactor by esterification of
one or more carboxylic acids of formula (III)

with
one or more alcohols R2-OH,
wherein
said one or more carboxylic acids of formula (III) used in the esterification, or a portion thereof, is obtained in step (A-2)
and/or
said one or more alcohols R2-OH used in the esterification, or a portion thereof, is obtained in step (A-2).

The term "esterification" indicates reaction conditions suitable for causing a reaction between carboxylic acid of formula (III) with alcohols R2-OH to give carboxylic acid esters of formula (II).

As mentioned above, in this specific aspect of the present invention and in all corresponding statements regarding preferred embodiments or features, group R1 is the very same in the compounds of formula (I), (II) and (III).

Similarly, in this specific aspect of the present invention and in all corresponding statements regarding preferred embodiments or features, group R2 is the very same in the compounds of formula (II) and alcohol R2-OH.

Due to the intrinsic chemistry of a process of the invention, group R1 as provided in carboxylic acid esters of formula (II) in the resulting mixture of step (A-2) is present in the carboxylic acids of formula (III) and is present in HMF esters of formula (I), and similarly group R2 as provided in carboxylic acid esters of formula (II) in the resulting mixture of step (A-2) is present in alcohol R2-OH.

The term "in a separate reactor" in the specific aspect of the invention above indicates that the esterification of one or more carboxylic acids of formula (III) with one or more alcohols R2-OH to one or more carboxylic acid esters of formula (II) is not conducted in the same reactor in which the reaction of step (A-2) is conducted, but in a separate reactor.

As mentioned above, the invention relates to a process for preparing furan-2,5-dicarboxylic acid as described above, wherein said process comprises step (B-1).

If, in step (B-1), a mixture comprising 5-(hydroxymethyl) furfural and/or one or more HMF esters of formula (I) obtained from said mixture resulting in step (A-2) by additional treatment steps is subjected to oxidation conditions, said additional treatment steps preferably comprise a step of filtering the mixture resulting in step (A-2), in order to separate solid particles, e.g. humins, from a liquid phase.

It is an achievement of the present invention that the (co-)solvent for the oxidation reaction in step (B-1) is produced in step (A-2) before. Therefore, typically, no additional solvent or only a mass of solvent, which is smaller than the mass of carboxylic acid of formula (III) present in the mixture after step (A-2) is added between step (A-2) and step (B-1). Moreover, costly storage units for solvents, more precisely for acidic solvents, for the oxidation reaction in step (B-1) are not necessary in a process for preparing furan-2,5-dicarboxylic acid according to the present invention.

In particular, a process for preparing furan-2,5-dicarboxylic acid according to the present invention as described above or below is preferred, wherein said additional treatment steps comprise (A-3) separating by distillation from said mixture resulting in step (A-2)
at least a portion of the one or more alcohols R2-OH
and/or
at least a portion of the remaining fraction of said amount of one or more carboxylic acid esters of formula (II).

Preferred is also a process for preparing furan-2,5-dicarboxylic acid according to the present invention as described herein above or below, wherein said additional treatment steps comprise (A-3-a) separating by distillation from said mixture resulting in step (A-2)
at least 50 wt.-%, preferably at least 90 wt.-%, more preferably at least 99 wt.-% of the total weight of said one or more alcohols R2-OH
and/or
at least 50 wt.-%, preferably at least 90 wt.-%, more preferably at least 99 wt.-% of the total weight of the remaining fraction of said amount of one or more carboxylic acid esters of formula (II).

When distilling a portion of the one or more alcohols R2-OH and a portion of the remaining fraction of said amount of one or more carboxylic acid esters of formula (II) from said mixture resulting in step (A-2), the carboxylic acids of formula (III) remain and can be used as the predominant solvent for step (B-1). They are preferred (co-)solvents for the oxidation to FDCA and lead to an increased yield in FDCA in step (B-1).

A process for preparing furan-2,5-dicarboxylic acid according to the present invention as described above or below is preferred, wherein said
one or more carboxylic acid esters of formula (II)

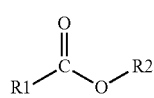

(II)

present in said starting mixture prepared or provided in step (A-1) is prepared in a separate reactor by esterification of one or more carboxylic acids of formula (III)

(III)

with
one or more alcohols R2-OH,
wherein
said one or more carboxylic acids of formula (III) used in the esterification, or a portion thereof, is recycled from the product mixture resulting from step (B-1)
and/or
said one or more alcohols R2-OH used in the esterification, or a portion thereof, is recycled from the distillate of step (A-3) or (A-3-a).

As mentioned above, in this specific aspect of the present invention and in all corresponding statements regarding preferred embodiments or features, group R1 is the very same in the compounds of formula (I), (II) and (III).

Similarly, in this specific aspect of the present invention and in all corresponding statements regarding preferred embodiments or features, group R2 is the very same in the compounds of formula (II) and alcohol R2-OH.

Due to the intrinsic chemistry of a process of the invention, group R1 as provided in carboxylic acid esters of formula (II) in the resulting mixture of step (A-2) is present in the carboxylic acids of formula (III) and is present in HMF esters of formula (I), and similarly group R2 as provided in carboxylic acid esters of formula (II) in the resulting mixture of step (A-2) is present in alcohol R2-OH.

The term "recycled from" indicates, for example, a separation by distillation from a mixture as described herein above followed by refeeding the distillate to an upstream process step, e.g. to the preparation of the starting mixture as, for example, in step (A-1).

The term "distillate" indicates the amount of a substance, which has been evaporated from a mixture by means of distillation, for example, from a mixture resulting in step (A-2).

The term "in a separate reactor" in the specific aspect of the invention above indicates that the esterification of one or more carboxylic acids of formula (III) with one or more alcohols R2-OH to one or more carboxylic acid esters of formula (II) is not conducted in the same reactor in which the reaction of step (A-2), or the oxidation reaction of step (B-1) is conducted, but in a separate reactor.

By reusing carboxylic acid esters of formula (II) and alcohol R2-OH recycled from the distillate of step (A-3) or (A-3-a) as well as carboxylic acids of formula (III) recycled from the product mixture resulting from step (B-1), a mixture mainly comprising carboxylic acid esters of formula (II) is prepared which can be used for preparing the starting mixture in step (A-1). Therewith the amount of waste products is decreased.

Furthermore, a process for preparing furan-2,5-dicarboxylic acid according to the present invention as described above or below is preferred, wherein at least 90% by weight of the total amount of said one or more carboxylic acids of formula (III)

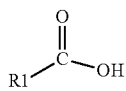

(III)

as obtained in step (A-2) is present in the mixture subjected to oxidation conditions in step (B-1).

By having 90% by weight of the total amount of said one or more carboxylic acids of formula (III) as obtained in step (A-2) present in the mixture subjected to oxidation conditions in step (B-1), the carboxylic acids of formula (III) are used as a relevant (co-)solvent for step (B-1). The carboxylic acids of formula (II) are preferred solvents for the oxidation to FDCA and leads to an increased yield in FDCA in step (B-1).

Moreover, a process for preparing furan-2,5-dicarboxylic acid according to the present invention as described above or below is preferred, wherein between steps (A-2) and (B-1)
(i) there is no solvent change step
or
(ii) no carboxylic acid of formula (III) is removed, but an additional amount of one, two or more carboxylic acids of formula (III) is added, wherein preferably at least one of said one, two or more carboxylic acids of formula (III) is selected from the group consisting of formic acid and acetic acid, wherein preferably one of said one, two or more carboxylic acids of formula (III) is acetic acid.

By using carboxylic acid esters of formula (II) as solvent in step (A-2), carboxylic acids of formula (III) are formed which serve as very good solvent in oxidation step (B-1). Therefore, no further type of solvent needs to be added reducing the complexity of reactor set-ups compared to processes known in the prior art. Thus, preferably in a process of the present invention (in particular in a process as described above as being preferred) one or more specific carboxylic acids of formula (III) are formed in step (A-2) and no amount of said specific carboxylic acid(s) of formula (III) is(are) removed between steps (A-2) and (B-1), but in some preferred cases an additional amount of said specific carboxylic acid(s) of formula (III) is added between steps (A-2) and (B-1), wherein preferably no other organic acid, more preferably no other organic compound, is added, and preferably no water is added. Thus, the chemical constitution of the solvent or solvent mixture used in step (B-1) is significantly determined by said one or more carboxylic acid esters of formula (II) which are hydrolyzed to give said one or more carboxylic acids of formula (III), respectively.

In case no solvent change step is conducted at all between steps (A-2) and (B-1) the complexity of reactor set-ups is reduced compared to processes known in the prior art.

Preferred is also a process for preparing furan-2,5-dicarboxylic acid according to the present invention as described above or below, wherein said mixture subjected to oxidation conditions in step (B-1) comprises
one, two or all substances selected from the group consisting of
cobalt,
manganese,
cerium,
zirconium,
and
bromide.

Substances as described above accelerate the conversion of HMF and/or HMF esters of formula (I) to FDCA. Further suitable catalysts are disclosed in the literature, see, e.g., "Methodology and scope of metal/bromide autoxidation of hydrocarbons", Catalysis Today 23 (1995) 69-158.

A process for preparing furan-2,5-dicarboxylic acid according to the present invention as described above or below is preferred, wherein the mass ratio of the total amount of said one or more carboxylic acids of formula (III) in the product mixture resulting in step (B-1) to the total amount of said one or more carboxylic acids of formula (III) in the mixture subjected to oxidation conditions in step (B-1) is >0.85, preferably >0.9, more preferably >0.99. In practice, said mass ratio depends from the oxidation conditions chosen in step (B-1). Preferably, the conditions are chosen so that said carboxylic acids of formula (III) which are present as a solvent in the mixture subjected to oxidation conditions are not oxidized. In practice, the skilled person by routine experimentation will identify mild conditions which allow for the oxidation of 5-(hydroxymethyl)furfural and/or one or more HMF esters of formula (I) without simultaneously oxidizing said carboxylic acids of formula (III).

The more carboxylic acids of formula (III) remains in the product mixture resulting in step (B-1) the more carboxylic acids of formula (III) can be recycled making a process according to the present invention more efficient and environmentally friendly.

Preferably, at least 90% by weight of the total amount of said one or more carboxylic acids of formula (III) as present in the mixture resulting in step (A-2), and preferably at least 90% by weight of the total amount of said one or more carboxylic acids of formula (III) as present in the mixture subjected to oxidation conditions in step (B-1) of the process of the present invention for preparing furan-2,5-dicarboxylic acid are present in the product mixture resulting from step (B-1) comprising furan-2,5-dicarboxylic acid and one or more carboxylic acids of formula (III). The skilled person selects the oxidation conditions in step (B-1), and in particular the oxidation catalyst typically used (see above) in step (B-1), in order to selectively oxidize HMF and HMF ester of formula (I) rather than said one or more carboxylic acids of formula (III).

The invention also relates to the use of a carboxylic acid ester of formula (II),

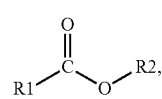

(II)

wherein in each of said carboxylic acid esters of formula (II)
R1 is
(i) hydrogen
or
(ii) a substituted or unsubstituted, branched or linear, saturated or unsaturated or aromatic hydrocarbon radical having a total
and
R2 is a substituted or unsubstituted, branched or linear or cyclic, aliphatic hydrocarbon radical having a total number of 10 carbon atoms or less,
in a process for preparing furan-2,5-dicarboxylic acid from carbohydrate compounds as described above,
as the solvent or as a co-solvent for said carbohydrate compounds
and
as dehydration agent.

Disclosed herein is also the corresponding use of a carboxylic acid ester of formula (II) in a process for preparing 5-(hydroxymethyl)furfural and HMF esters of formula (I)

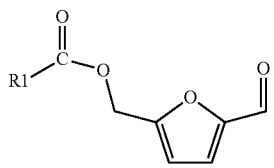

(I)

wherein R1 is
(i) hydrogen
or
(ii) a substituted or unsubstituted, branched or linear, saturated or unsaturated or aromatic hydrocarbon radical having a total number of 21 carbon atoms or less,
from carbohydrate compounds as described above
as the solvent or as a co-solvent for said carbohydrate compounds
and
as dehydration agent.

Generally, all aspects and definitions discussed herein above in the context of a process for preparing a mixture comprising HMF or one or more HMF esters of formula (I) and of a process for preparing furan-2,5-dicarboxylic acid according to the present invention apply mutatis mutandis to the use of a carboxylic acid ester of formula (II). And likewise, all aspects of the inventive use of a carboxylic acid ester of formula (II) discussed herein above or below apply mutatis mutandis to a process for preparing a mixture comprising HMF and one or more HMF esters of formula (I) and to a process for preparing furan-2,5-dicarboxylic acid according to the present invention.

As mentioned above, in many industrial cases it is preferred to employ alkyl formates of the formula R2-O—C(=O)H (as for alternative (i), meaning R1=H) as they are readily available. However, in other cases, where R1 is hydrocarbon radical as defined herein above or below (as for alternative (ii), the corresponding carboxylic acid esters of formula (II) are preferred over said alkyl formates of the formula R2-O—C(=O)H.

As HMF is esterified to HMF ester of formula (I) in the overall reaction scheme carboxylic acid esters of formula (II) also act as esterification agents. Therefore, according to the present invention, carboxylic acid esters of formula (II) can also be used as esterification agent for HMF in a process for preparing 5-(hydroxymethyl)furfural and HMF esters of formula (I) and in a process of the present invention for preparing furan-2,5-dicarboxylic acid.

Preferred is the use of a carboxylic acid ester of formula (II),
wherein R1 is
(i) hydrogen (preferred in specific industrial cases)
or
(ii) a linear or branched, saturated or unsaturated hydrocarbon radical having 15 carbon atoms or less,
more preferably a linear or branched, saturated or unsaturated hydrocarbon radical having 8 carbon atoms or less,
even more preferably a linear or branched, aliphatic radical having 6 carbon atoms or less,
particularly more preferably —CH$_3$, —CH$_2$CH$_3$, —CH(CH$_3$)CH$_3$, —C(CH$_3$)$_3$, —CH$_2$CH$_2$CH$_3$, or —CH$_2$CH$_2$CH$_2$CH$_3$,
most preferably —CH$_3$,
and/or
R2 is
a substituted or unsubstituted, branched or linear or cyclic, alkyl radical having a total number of 10 carbon atoms or less,
preferably a substituted or unsubstituted, branched or linear or cyclic, alkyl radical having a total number of 6 carbon atoms or less,
more preferably a unsubstituted alkyl radical selected from the group consisting of methyl, ethyl, prop-1-yl, propan-2-yl, butan-1-yl, butan-2-yl, pentan-1-yl, pentan-2-yl, pentan-3-yl, 2-methylpropan-1-yl, 2-methylpropan-2-yl, 2-methylbutan-1-yl, 3-methylbutan-1-yl, 2-methylbutan-2-yl, 3-methylbutan-2-yl, cyclopentyl, and cyclohexyl,
even more preferably methyl.

As mentioned above, in some industrial cases it is preferred to employ alkyl formates of the formula R2-O—C(=O)H (as for alternative (i), meaning R1=H) as they are readily available. However, in other cases, where R1 is hydrocarbon radical as defined herein above or below (as for alternative (ii)), the corresponding specific carboxylic acid esters of formula (II) as described in the specific aspect above are preferred over said alkyl formates of the formula R2-O—C(=O)H.

Particularly preferred is the use of a carboxylic acid ester of formula (II), wherein said one or at least one, preferably all, of said more carboxylic acid esters of formula (II) is
selected from the group consisting of methyl formate, ethyl formate, butyl formate methyl acetate, ethyl acetate, and butyl acetate,
preferably selected from the group consisting of methyl acetate, ethyl acetate, and butyl acetate,
more preferably methyl acetate.

As mentioned above, in some industrial cases it is preferred to employ alkyl formates of the formula R2-O—C(=O)H (as for alternative (i), meaning R1=H) as they are readily available. However, in other cases, where R1 is hydrocarbon radical as defined herein above or below (as for alternative (ii), the corresponding specific carboxylic acid esters of formula (II) as defined in the specific aspect above are preferred over said alkyl formates of the formula R2-O—C(=O)H.

Hereinafter, the invention will be explained in some more detail with reference to the attached drawings.

FIGURES

FIG. 1:
FIG. 1 is a schematic drawing of typical reactions taking place in an exemplary process of the present invention.

In FIG. 1 the term "fructose/glucose" is used to designate an example of said "one, two or more carbohydrate compounds selected from the group consisting of hexoses, oligosaccharides comprising hexose units, and polysaccharides comprising hexose units" present in the starting mixture prepared or provided in process step (A-1).

"MeOAc" indicates methyl acetate and correspondingly designate an example of said "one or more carboxylic acid esters of formula (II)" as present in the starting mixture prepared or provided in step (A-1).

According to the first reaction depicted in FIG. 1, fructose/glucose is subjected to reaction conditions so that HMF is formed. MeOAc is the solvent for fructose/glucose according to the first reaction of FIG. 1. Three equivalents of water are produced when fructose/glucose is transformed into HMF.

According to the second reaction depicted in FIG. 1, MeOAc reacts with water (e.g. water as produced by the reaction of fructose/glucose to HMF) and as a result acetic acid as well as methanol (MeOH) is formed.

According to the third reaction depicted in FIG. 1 HMF reacts with acetic acid (AcOH) to give the corresponding HMF ester (acetylated HMF; i.e., an HMF ester of formula (I) with $R1=CH_3$)

Summarizing, fructose/glucose and MeOAc (which acts both as a solvent and a reaction partner) react to give acetylated HMF (as an example of an HMF ester of formula (I)) as well as methanol (as an example of an alcohol R2-OH) and acetic acid (AcOH; an example of a carboxylic acid of formula (III)). Furthermore produced are three equivalents of water. As HMF produced by dehydration of fructose/glucose is typically not reacted quantitatively with acetic acid in a typical scenario the reaction product mixture also comprises HMF.

Fructose/glucose as well as MeOAc are considered to be compounds of the starting mixture prepared or provided in step (A-1) of the present invention.

HMF, the HMF ester (acetylated HMF), acetic acid and methanol as well as a remaining fraction of MeOAc are considered as components of the mixture resulting in process step (A-2). In schematic FIG. 1 MeOAc is not depicted on the right hand side of any of the reactions shown, as the major amount of MeOAc is reacted.

Figure 2:
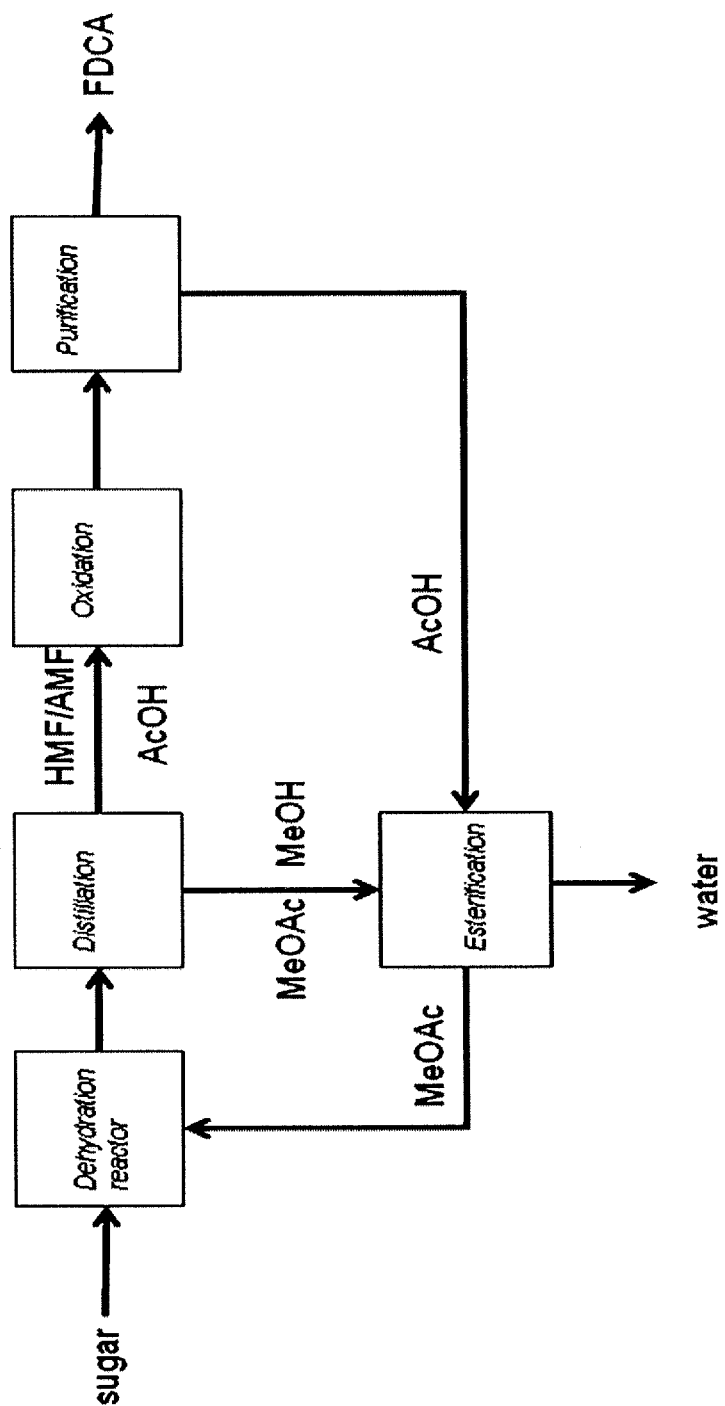
FIG. 2 is a schematic drawing of exemplary process steps conducted in a process of the present invention.

FIG. 2:

FIG. 2 is a schematic drawing of typical (exemplary) process steps conducted in a process of the present invention.

In FIG. 2, the term "sugar" is used to indicate an example of said "one, two or more carbohydrate compounds selected from the group consisting of hexoses, oligosaccharides comprising hexose units, and polysaccharides comprising hexose units" present in the starting mixture prepared or provided in process step (A-1).

The sugar is first dehydrated in a dehydration reactor which is co-fed with MeOAc (methyl acetate as an example of a carboxylic acid ester of formula (II)). In the dehydration reactor, a mixture results comprising HMF and/or 5-(acetoxymethyl)furfural (AMF, as an example of a HMF ester of formula (I)), methanol (as an example of an alcohol R2-OH), acetic acid (as an example of a carboxylic acid of formula (III)) and a remaining fraction of methyl acetate.

The resulting mixture (corresponding to a mixture resulting in step (A-2) according to the present invention) is subsequently distilled in order to remove methyl acetate and methanol.

After separating methanol and methyl acetate from the mixture comprising the remaining compounds
   (i) acetic acid,
   and
   (ii) HMF and/or AMF,
   to said mixture,
   (iii) more acetic acid
   can optionally added if needed (not shown in FIG. 2).

Subsequently said mixture comprising (i) acetic acid, and (ii) HMF and/or AMF and (iii) optionally additional acetic acid is subjected to oxidation conditions (according to step (B-1)) in order to give a product mixture comprising FDCA and acetic acid.

In a final purification step, the FDCA is separated from the acetic acid remaining after the oxidation reaction in step (B-1).

The separated acetic acid is subsequently esterified to methyl acetate by reaction with the methanol, which has been separated together with methyl acetate in the distillation step prior to the oxidation. In said esterification step, water is formed as a co-product, and disposed. A resulting mixture mainly comprises methyl acetate and is recycled into the dehydration reactor.

Thus, in the overall process scheme in FIG. 2, sugars are converted into purified FDCA with water being the only relevant by-product produced in the overall process in significant amounts.

Hereinbelow, the invention is described in more detail by examples:

Examples

Quantification Method:

Quantification by GC:

The quantification of products has been done by GC-analysis with a Agilent Technologies 6890N GC with 7693 Autosampler and a 5973 MSD (Column: VF624 ms with dimensions of 60 m*0.25 mm*1.4 µm. The different GC set-up parameters have been: injection volume: 1 µL. Inlet: 200° C., Split: 60:1, Flow: 0.8 ml/min constant flow. Oven: start temp: 50° C.; 3° C./min to 300° C. hold for 7 minutes)

Experiments 1 to 24: Reaction Parameter Screening

Experimental Procedure of Screening Experiments 1 to 24:

Screening was carried out in a series of single experiments designated "Experiment 1" to "Experiment 24".

In each single experiment "1" to "24", one or more carbohydrate compounds according to the present invention was at least partially converted into HMF and 5-(acetoxymethyl)furfural (as an example of a carboxylic acid ester of formula (I) according to the present invention) in methyl acetate (MeOAc, solvent used as an example of a carboxylic acid ester of formula (II) according to the present invention).

The general experimental procedure for each screening experiment of "1" to "24" was as follows:

In a first step (as an example of step (A-1) of a process according to the invention), a starting mixture was prepared by filling 60 g of methyl acetate, a specific amount of fructose (see experiments 1 to 12 in table 1 and experiments 21 to 24 in table 3 below) or an aqueous fructose syrup with at least 66.5 wt-% fructose and some glucose (see experiments 13 to 20 in table 2 below).

and a catalyst (also designated as "additive", only for experiments 9 to 13 and 15 to 20)

into a steel autoclave reactor (inner volume 300 ml).

The amounts of fructose or fructose syrup were in the range of from:

Fructose: 3.0-12.0 g (see table 1 below);
Fructose syrup: 6.0-38.0 g (see table 2 below).

In a second step (as an example of step (A-2) of a process according to the invention), the filled steel autoclave reactor was tightly sealed and pressurized with nitrogen (total pressure 50 bar) and the reaction mixture inside the steel autoclave reactor was heated to a temperature of 100-240° C. (see table 1, 2 and 3 below) while stirring at 1000 rpm. After the corresponding reaction temperature was reached, the reaction temperature was maintained for 1-40 hours (see table 1, 2 and 3 below) while continuing stirring the reaction mixture inside the heated and pressurized steel autoclave reactor.

Subsequently, the steel autoclave reactor was
(i) allowed to cool down to room temperature (approximately 22° C.),
(ii) the pressure was released,
and
(iii) the steel autoclave reactor was opened.

For further analysis, 1 mL of the resulting mixture comprising HMF, 5-(acetoxymethyl)furfural, acetic acid, methanol and a remaining fraction of the initially added 60 g of the MeOAc was subjected to GC analysis to quantify said reaction products.

Yield:

$$\text{HMF yield}[\%] = n_{HMF}/n_{Fructose}$$

$$\text{AMF yield}[\%] = n_{AMF}/n_{Fructose}$$

$$\text{Di-HMF yield}[\%] = (n_{Di\text{-}HMF} \times 2)/n_{Fructose}$$

$$\text{Furfural yield}[\%] = n_{Furfural}/n_{Fructose}$$

$$\text{overall yield}[\%] = \text{HMF yield}[\%] + \text{AMF yield}[\%] + \text{Di-HMF yield}[\%]$$

If not indicated otherwise, molar amounts and the corresponding yields are calculated on the basis of GC data.

Experimental Results of the Screening Experiments Described Above (1-23) According to the Present Invention:

In table 1 and 2, the reaction time, the reaction temperature, the type and amount of catalyst used, the initial amount of fructose (table 1) or the initial amount of fructose syrup (table 2), respectively, the HMF yield, AMF yield, di-HMF yield, furfural yield and the overall yield of each single experiment of the screening experiments 1 to 23 described above are shown.

TABLE 1

Experimental parameters and yield of catalyst screening experiments with (i) fructose as carbohydrate compound of the present invention and (ii) 60 g of MeOAc as a carboxylic acid ester of the present invention.

| Exp. | T [° C.] | time [h] | type of catalyst/ corresponding weight [g] | Fructose [g] | HMF yield [%] | AMF yield [%] | Di-HMF yield [%] | Furfural yield [%] | overall yield [%] |
|---|---|---|---|---|---|---|---|---|---|
| 1 | 200 | 2 | — | 3 | 7.9 | 0.6 | 1.0 | 1.8 | 26.4 |
| 2 | 200 | 5 | — | 3 | 6.9 | 2.4 | 1.2 | 1.9 | 27.5 |
| 3 | 200 | 5 | — | 6 | 11.4 | 12.7 | 2.6 | 4.1 | 35.3 |
| 4 | 200 | 5 | — | 12 | 19.6 | 18.7 | 2.4 | 8.6 | 40.6 |
| 5 | 180 | 16 | — | 12 | 12.2 | 20.7 | 2.0 | 5.6 | 34.9 |
| 6 | 180 | 16 | — | 6 | 18.1 | 19.6 | 1.6 | 5.6 | 39.4 |
| 7 | 160 | 16 | — | 6 | 20.7 | 1.9 | 0.6 | 1.2 | 34.4 |
| 8 | 140 | 16 | — | 6 | 12.2 | 0.1 | 0.1 | 0.5 | 19.3 |
| 9 | 200 | 16 | LiCl/ 0.023 | 3 | 10.3 | 29.9 | 0.4 | 1.8 | 40.5 |
| 10 | 220 | 2 | LiCl/ 0.141 | 12 | 21.9 | 23.2 | 0.8 | 1.5 | 45.9 |
| 11 | 220 | 2 | NaCl/ 0.195 | 12 | 23.9 | 23.0 | 0.8 | 1.8 | 47.7 |
| 12 | 200 | 16 | FeCl$_3$/ 0.135 | 3 | 0.6 | 2.4 | 0.2 | 8.6 | 3.2 |

When comparing the overall yield of Experiments 1 to 8 with Experiments 9 to 12, it can be seen that reactions with LiCl or NaCl as a catalyst have an increased overall yield. Thus, using LiCl or NaCl as a catalyst is preferred.

A comparison between Experiments 1 and 2 shows that more AMF is produced when the duration of the reaction is increased. Thus, a longer duration of the reaction is preferred to yield more AMF.

When changing the initial amount of fructose from 3 to 12 g at constant reaction time and constant reaction temperature, the overall yield is increased (see experiments 2 to 4). Thus an amount of fructose in the starting mixture up to 20 wt.-% is preferred in order to increase the overall yield.

In experiments 6 to 8, the reaction temperature is decreased from 180° C. to 140° C. while the remaining parameters are kept constant. As a consequence, the AMF yield is increased up to 19.9% (at 180° C.). As a result, the ratio of HMF to AMF is decreased with increasing reaction temperature. Thus, high reaction temperatures are preferred.

In experiments 9 to 12, three different catalysts were added to the starting mixture. The overall yield was increased when LiCl and NaCl (experiments 10 and 11) were used as a catalyst but decreased when FeCl$_3$ was used instead (experiment 10 vs. 13). Thus, alkali halides are preferred over other metal halides.

TABLE 2

Experimental parameters and yield of catalyst screening experiments with
(i) fructose syrup as carbohydrate compounds of the present invention
and
(ii) 60 g of MeOAc as a carboxylic acid ester of the present invention.

| Exp. | T [° C.] | time [h] | NaCl [g] | Fructose syrup [g] | HMF yield [%] | AMF yield [%] | Di-HMF yield [%] | Furfural yield [%] | overall yield [%] |
|---|---|---|---|---|---|---|---|---|---|
| 13 | 220 | 2 | 0.19 | 12 | 41.2 | 22.4 | 0.4 | 1.7 | 64.1 |
| 14 | 220 | 2 | — | 12 | 24.3 | 18.2 | 1.2 | 9.9 | 43.7 |
| 15 | 200 | 1 | 0.19 | 12 | 38.4 | 11.6 | 0.4 | 1.1 | 50.4 |
| 16 | 200 | 2 | 0.19 | 12 | 37.9 | 19.0 | 0.2 | 1.3 | 57.1 |
| 17 | 200 | 4 | 0.19 | 12 | 36.8 | 22.4 | 0.2 | 1.2 | 59.4 |
| 18 | 200 | 4 | 0.39 | 6 | 19.3 | 19.4 | 0.2 | 11.9 | 38.9 |
| 19 | 200 | 4 | 0.19 | 24 | 29.9 | 10.7 | 0.4 | 1.1 | 41.0 |
| 20 | 200 | 4 | 0.19 | 36 | 24.5 | 6.3 | 0.4 | 1.1 | 31.2 |

Comparing the overall yield of experiment 13 (with NaCl as catalyst) to the overall yield of experiment 14 (without catalyst), a significant increase in the overall yield and in the selectivities was observed.

In experiments 15 to 17, the reaction time is changed from 1 h to 4 h at a constant initial concentration of fructose of 7.9 g and a constant reaction temperature of 200° C. An increase in the overall yield from 50.2% to 59.3% was measured with increasing reaction time. Thus, a longer duration of the reaction is preferred when using a catalyst.

In experiments 17 to 20, the initial concentration of fructose is changed from 3.7 to 32.3 g at a constant reaction time of 4 h and a constant reaction temperature of 200° C. The overall yield is increased to 59.3% when using 7.9 instead of 3.7. However, when increasing the initial concentration of fructose further to 32.3 g the overall yield decreases to 31.0%. Thus, the amount of fructose in the starting mixture in step (A-1) is preferably between 10 and 20 wt.-%.

Experiments 21 to 24: Specific Effect of Reaction Time and Reaction Temperature

In order to see the effect of the reaction time and reaction temperature in the dehydration step of the carbohydrate compounds (as in step (A-2) of the invention) on the molar ratio of HMF/AMF in a resulting mixture, experiments 21 to 24 have been conducted at different temperatures and/or different reaction times (see table 3).

TABLE 3

Effect of reaction time and reaction temperature in catalyst screening
experiments 23 to 26 with
(i) fructose as carbohydrate compounds of the present invention
and
(ii) 60 g of MeOAc as a carboxylic acid ester of the present invention.

| Exp. | T [° C.] | time [h] | catalyst [g] | Fructose [g] | Molar ratio of HMF to AMF |
|---|---|---|---|---|---|
| 21 | 200 | 16 | — | 3.0 | 0.50 |
| 22 | 160 | 16 | — | 3.0 | 6.75 |
| 23 | 200 | 40 | — | 3.0 | 0.23 |
| 24 | 240 | 16 | — | 3.0 | 0.27 |

The results of experiments 21 to 24 show that the molar ratio HMF/AMF can be adjusted by selecting reaction time and reaction temperature, when using otherwise identical reaction conditions. When using temperatures of 200° C. and 240° C., respectively, the molar ratio HMF/AMF is significantly lower than at a reaction temperature of 160° C. (see Experiments 1, 3, 4 versus Experiment 2). A comparison of Experiments 1 and 3 shows that at the identical temperature of 200° C., the molar ratio HMF/AMF decreases when the duration of the reaction is increased. Thus, in order to arrive at a low molar ratio HMF/AMF it is preferred to employ a reaction temperature in the range of from 160 to 240° C.

The invention claimed is:

1. A process for preparing furan-2,5-dicarboxylic acid, the process comprising the following steps:
   (A-1) preparing or providing a starting mixture comprising:
      one, two, or more carbohydrate compounds selected from the group consisting of hexoses, oligosaccharides, and polysaccharides,
      and as a solvent or as a co-solvent for said carbohydrate compounds an amount of one or more carboxylic acid esters of a formula (II)

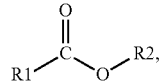

(II)

wherein for each of said carboxylic acid esters of formula (II):
R1 is hydrogen or a branched or linear, saturated or unsaturated or aromatic hydrocarbon radical having a total number of 21 carbon atoms or less, and
R2 is a branched or linear or cyclic, aliphatic hydrocarbon radical having a total number of 10 carbon atoms or less,
(A-2) subjecting said starting mixture to reaction conditions such that at least one of said one, two, or more carbohydrate compounds reacts, and a fraction of said amount of one or more carboxylic acid esters of formula (II) is hydrolyzed, such that a mixture results comprising:
5-(hydroxymethyl)furfural and/or one or more HMF esters of formula (I)

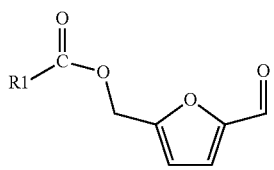
(I)

wherein for each of said HMF esters of formula (I), independently of each other, R1 is
(i) hydrogen or
(ii) a branched or linear, saturated or unsaturated or aromatic hydrocarbon radical having a total number of 21 carbon atoms or less,
one or more carboxylic acids of a formula (III)

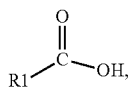
(III)

wherein R1 is the same as defined for formula (I) above,
one or more alcohols R2-OH, wherein R2 is the same as defined for formula (II) above, and
a remaining fraction of said amount of one or more carboxylic acid esters of formula (II),
(B-1) subjecting
said mixture resulting in step (A-2) or
a mixture comprising 5-(hydroxymethyl)furfural and/or one or more HMF esters of formula (I) obtained from said mixture resulting in step (A-2) by additional treatment steps
to oxidation conditions such that a product mixture results comprising furan-2,5-dicarboxylic acid and one or more carboxylic acids of formula (III).

2. The process according to claim 1, wherein for the mixture resulting in step (A-2), a total amount of 5-(hydroxymethyl)furfural and HMF esters of formula (I) is in the range of from 0.5 to 50 wt.-% based on a total weight of the mixture resulting in step (A-2), and/or wherein a total weight of the one, two, or more carbohydrate compounds in the starting mixture prepared or provided in step (A-1) is in the range of from 1 to 70 wt % based on the total weight of the starting mixture.

3. The process according to claim 1, wherein the starting mixture prepared or provided in step (A-1) comprises fructose and glucose, and/or comprises less than 35 wt % of water based on a total weight of the starting mixture, and/or has an acid value below 50 and/or
comprises a total amount of carboxylic acid esters of formula (II) of at least 10 wt. %, based on the total weight of the starting mixture.

4. The process according to claim 1, wherein for the mixture resulting in step (A-2), a molar ratio of the amount of 5-(hydroxymethyl)furfural to a total amount of HMF esters of formula (I) is in the range of from 100 to 0.001, and/or wherein said subjecting said starting mixture to reaction conditions of step (A-2) comprises subjecting said starting mixture to a reaction temperature for at least 10 minutes, the reaction temperature in the range of from 70° C. to 300° C. and/or wherein in step (A-2) the reaction temperature is in the range of from 185° C. to 220° C.

5. The process according to claim 1, wherein said one or at least one of said more alcohols R2-OH:
(i) has a vapor pressure of at least 0.1 kPa at 25° C., and/or
(ii) is selected from the group consisting of: methanol, ethanol, 1-propanol, 2-propanol, 1-butanol, 2-butanol, 1-hydroxy-2-methylpropan, 2-hydroxy-2-methylpropan, and 2-Methoxy ethanol.

6. The process according to claim 1, wherein R1 is:
(i) hydrogen or
(ii) a linear or branched, saturated or unsaturated hydrocarbon radical having 15 carbon atoms or less.

7. The process according to claim 1, wherein said one or at least one of said carboxylic acid esters of formula (II) is selected from the group consisting of methyl formate, ethyl formate, butyl formate, methyl acetate, ethyl acetate, and butyl acetate.

8. The process according to claim 1, wherein a molar ratio of a total amount of said carboxylic acid esters of formula (II) present in the starting mixture prepared or provided in step (A-1) to a total amount of water
(i) present in the starting mixture prepared or provided in step (A-1) and
(ii) produced in step (A-2) by reaction of said carbohydrate compounds selected from the group consisting of hexoses, oligosaccharides, and polysaccharides is above 1.

9. The process according to claim 1, wherein said starting mixture prepared or provided in step (A-1) comprises water, wherein the molar ratio of a total amount of said carboxylic acid esters of formula (II) to water is above 3, and/or wherein said starting mixture prepared or provided in step (A-1) comprises water, wherein in said starting mixture the molar ratio of the total amount of said carboxylic acid esters of formula (II) to the sum of the total amount of water plus three times the total amount of hexoses and hexose units is above 1.

10. The process according to claim 1, wherein the starting mixture prepared or provided comprises a catalytically effective amount of one, two, or more catalysts being an alkali halide.

11. The process according to claim 1, wherein said one or more carboxylic acid esters of formula (II)

(II)

present in said starting mixture prepared or provided in step (A-1) is prepared in a separate reactor by esterification of
one or more carboxylic acids of formula (III)

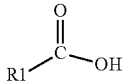
(III)

with one or more alcohols R2-OH, wherein said one or more carboxylic acids of formula (III) used in the esterification, or a portion thereof, is obtained in step (A-2) and/or said one or more alcohols R2-OH used in the esterification, or a portion thereof, is obtained in step (A-2).

12. The process for preparing furan-2,5-dicarboxylic acid according to claim 1, wherein said additional treatment steps comprise:
(A-3) separating, by distillation from said mixture resulting in step (A-2):
at least a portion of the one or more alcohols R2-OH, and/or
at least a portion of the remaining fraction of said amount of one or more carboxylic acid esters of formula (II).

13. The process according to claim 1, wherein at least 90% by weight of the total amount of said one or more carboxylic acids of formula (III)

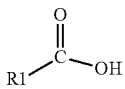
(III)

as obtained in step (A-2) is present in the mixture subjected to oxidation conditions in step (B-1), and/or
wherein between steps (A-2) and (B-1):
(i) there is no solvent change step, or
(ii) no carboxylic acid of formula (III) is removed, and an additional amount of one, two, or more carboxylic acids of formula (III) is added.

14. A method of using carboxylic acid ester of formula (II) defined in claim 1

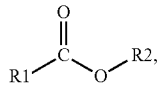
(II)

wherein R1 and R2 are defined in claim 1,
in a process for preparing furan-2,5-dicarboxylic acid

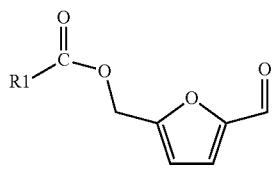
(I)

wherein R1 is the same as in the carboxylic acid ester of formula (II),
from said carbohydrate compounds defined in claim 1,
as a solvent or as a co-solvent for said carbohydrate compounds, and
as a dehydration agent.

15. The process according to claim 2, wherein for the mixture resulting in step (A-2), the total amount of 5-(hydroxymethyl)furfural and HMF esters of formula (I) is in the range of from 5 to 30 wt. %.

16. The process according to claim 4, wherein for the mixture resulting in step (A-2), the molar ratio of the amount of 5-(hydroxymethyl)furfural to the total amount of HMF esters of formula (I) is in the range of from 10 to 0.1.

17. The process according to claim 6, wherein R1 is:
(i) hydrogen or
(ii) a linear or branched, saturated or unsaturated hydrocarbon radical having 8 carbon atoms or less.

18. The process according to claim 7, wherein said one or at least one of said carboxylic acid esters of formula (II) is selected from the group consisting of methyl acetate, ethyl acetate, and butyl acetate.

19. The process according to claim 10, wherein the starting mixture prepared or provided comprises a catalytically effective amount of one, two, or more catalysts being a sodium halide or lithium halide.

* * * * *